(12) United States Patent
Dandekar et al.

(10) Patent No.: US 6,878,654 B2
(45) Date of Patent: Apr. 12, 2005

(54) REACTIVATION OF AROMATICS ALKYLATION CATALYSTS

(75) Inventors: Ajit B. Dandekar, South Plainfield, NJ (US); Michael Hryniszak, Bordentown, NJ (US); Jeffrey S. Beck, Clinton, NJ (US); David L. Stern, Annandale, NJ (US); Kathleen M. Keville, Beaumont, TX (US)

(73) Assignee: ExxonMobil Chemical Patents Inc., Houston, TX (US)

( * ) Notice: Subject to any disclaimer, the term of this patent is extended or adjusted under 35 U.S.C. 154(b) by 125 days.

(21) Appl. No.: 10/243,572

(22) Filed: Sep. 13, 2002

(65) Prior Publication Data

US 2003/0050521 A1 Mar. 13, 2003

Related U.S. Application Data

(63) Continuation-in-part of application No. 09/903,476, filed on Jul. 11, 2001.

(51) Int. Cl.$^7$ .............................. B01J 20/34; B01J 21/08
(52) U.S. Cl. ............................ 502/23; 502/26; 502/27; 502/28; 502/29; 502/33
(58) Field of Search .............................. 502/23, 26, 27, 502/28, 29, 33

(56) References Cited

U.S. PATENT DOCUMENTS

| | | | |
|---|---|---|---|
| 3,308,069 A | 3/1967 | Wadlinger et al. | 252/455 |
| 3,684,738 A | 8/1972 | Chen | 252/412 |
| 3,751,504 A | 8/1973 | Keown et al. | |
| 4,016,218 A | 4/1977 | Haag et al. | 260/671 R |
| 4,439,409 A | 3/1984 | Puppe et al. | 423/328 |
| 4,486,616 A * | 12/1984 | Chu et al. | 585/466 |
| 4,547,605 A | 10/1985 | Kresge et al. | 585/467 |
| 4,678,763 A | 7/1987 | Chang et al. | 502/26 |
| 4,826,667 A | 5/1989 | Zones et al. | 423/277 |
| 4,891,458 A | 1/1990 | Innes et al. | 585/323 |
| 4,954,325 A | 9/1990 | Rubin et al. | 423/328 |
| 4,992,606 A | 2/1991 | Kushnerick et al. | 585/467 |
| 5,001,094 A | 3/1991 | Chang et al. | 502/26 |
| 5,030,785 A | 7/1991 | Huss, Jr. et al. | 585/456 |
| 5,236,575 A | 8/1993 | Bennett et al. | 208/46 |
| 5,250,277 A | 10/1993 | Kresge et al. | 423/329.1 |
| 5,258,565 A | 11/1993 | Kresge et al. | 585/467 |
| 5,334,795 A | 8/1994 | Chu et al. | 585/467 |
| 5,362,697 A | 11/1994 | Fung et al. | 502/71 |
| 5,371,310 A | 12/1994 | Bennett et al. | 585/467 |
| 5,453,554 A | 9/1995 | Cheng et al. | 585/467 |
| 5,475,181 A * | 12/1995 | DiGuiseppi et al. | 585/510 |
| 5,536,895 A * | 7/1996 | Nair et al. | 585/480 |
| 5,612,270 A * | 3/1997 | Beck et al. | 502/64 |
| 5,695,736 A * | 12/1997 | Saxton et al. | 423/700 |
| 5,900,383 A | 5/1999 | Davis et al. | 502/22 |
| 5,900,520 A * | 5/1999 | Mazzone et al. | 585/467 |
| 5,990,032 A | 11/1999 | Wu et al. | 502/71 |
| 6,048,451 A * | 4/2000 | Huff et al. | 208/237 |

* cited by examiner

*Primary Examiner*—Stanley S. Silverman
*Assistant Examiner*—Jonas N. Strickland
(74) *Attorney, Agent, or Firm*—Darryl M. Tyus; Linda A. Kubena

(57) ABSTRACT

The present invention provides a process for regenerating a spent aromatics alkylation or transalkylation catalyst comprising a molecular sieve by contacting the spent catalyst with an oxygen-containing gas at a temperature of about 120 to about 600° C. and then contacting the catalyst with an aqueous medium, such as an ammonium nitrate solution, an ammonium carbonate solution or an acid solution.

12 Claims, No Drawings

REACTIVATION OF AROMATICS ALKYLATION CATALYSTS

This invention is a continuation-in-part of U.S. Ser. No. 09/903,476, filed Jul. 11, 2001.

BACKGROUND OF THE INVENTION

The present invention relates to a process for reactivating spent aromatics alkylation catalysts, and in particular the spent catalysts used in the alkylation and transalkylation steps of the liquid phase processes for the production of ethylbenzene and cumene.

Ethylbenzene and cumene are valuable commodity chemicals which are used industrially for the production of styrene monomer and phenol respectively. Ethylbenzene may be produced by a number of different chemical processes but one process which has achieved a significant degree of commercial success is the vapor phase alkylation of benzene with ethylene in the presence of a solid, acidic ZSM-5 zeolite catalyst. In the commercial operation of this process, the polyalkylated benzenes, including both polymethylated and polyethylated benzenes, which are inherently co-produced with ethylbenzene in the alkylation reactor, are transalkylated with benzene to produce additional ethylbenzene either by being recycled to the alkylation reactor or by being fed to a separate transalkylation reactor. Examples of such ethylbenzene production processes are described in U.S. Pat. Nos. 3,751,504 (Keown), 4,547,605 (Kresge), and 4,016,218 (Haag).

More recently, focus has been directed at liquid phase processes for producing ethylbenzene from benzene and ethylene since liquid phase processes operate at a lower temperature than their vapor phase counterparts and hence tend to result in lower yields of by-products. For example, U.S. Pat. No. 4,891,458 describes the liquid phase synthesis of ethylbenzene with zeolite beta, whereas U.S. Pat. No. 5,334,795 describes the use of MCM-22 in the liquid phase synthesis of ethylbenzene.

Cumene has for many years been produced commercially by the liquid phase alkylation of benzene with propylene over a Friedel-Craft catalyst, particularly solid phosphoric acid or aluminum chloride. More recently, however, zeolite-based catalyst systems have been found to be more active and selective for propylation of benzene to cumene. For example, U.S. Pat. No. 4,992,606 describes the use of MCM-22 in the liquid phase alkylation of benzene with propylene.

Other molecular sieves known for use as liquid phase alkylation and transalkylation catalysts include MCM-36 (see U.S. Pat. No. 5,258,565), MCM-49 (see U.S. Pat. No. 5,371,310) and MCM-56 (see U.S. Pat. No. 5,453,554).

Although MCM-22 and the related molecular sieves MCM-36, MCM-49 and MCM-56 are uniquely resistant to deactivation by coking, when used in liquid phase alkylation and transalkylation processes, they are susceptible to deactivation as a result of poisons, particularly nitrogen and sulfur compounds, in the feeds. In the past, this has required periodic ex-situ regeneration of the catalyst by contacting the spent catalyst at elevated temperature with flowing air so as to remove the deactivating species and burn off any coke deposits. However, although such air regeneration is effective in improving the activity of the catalyst, it tends to be accompanied by a decrease in the monoalkylation selectivity of the catalyst. This results in a significantly increased duty on the transalkylator and a consequent drop in overall yield and product purity. There is therefore a need for a regeneration protocol which minimizes this change in the selectivity of the catalyst to undesirable by-products.

According to the invention, it has now been found that contacting the air-regenerated catalyst with an aqueous medium is effective in restoring the selectivity of the catalyst back to its fresh state. In one desirable embodiment of this concept, the washing solution is an aqueous solution of ammonium nitrate or ammonium carbonate. In another desirable embodiment of this concept, the washing solution is an aqueous solution of acetic acid.

SUMMARY OF THE INVENTION

In one aspect, the invention resides in a process for regenerating a spent aromatics alkylation or transalkylation catalyst comprising a molecular sieve, the process comprising the steps of contacting the spent catalyst with an oxygen-containing gas at a temperature of about 120 to about 600° C. and then contacting the catalyst with an aqueous medium.

Preferably said aqueous medium is selected from the group consisting of an ammonium nitrate solution, an ammonium carbonate solution, a nitric acid solution, a hydrochloric acid solution, a sulfuric acid solution, a phosphoric acid solution, an oxalic acid solution, a salicyclic acid solution, a propionic acid solution, a benzoic acid solution, an acetic acid solution and mixtures thereof.

Preferably, the step of contacting the catalyst with an aqueous medium is conducted at a temperature of about 15 to about 120° C. for a period of about 10 minutes to about 48 hours.

Preferably, after contacting with the aqueous medium, the catalyst is calcined at a temperature of about 25 to about 600° C. for a period of about 10 minutes to about 48 hours.

In a further aspect, the present invention resides in a process for alkylating an aromatic compound comprising the steps of:
(a) contacting an alkylatable aromatic compound and an alkylating agent with an alkylation catalyst comprising a molecular sieve under alkylation conditions;
(b) when said alkylation catalyst has become at least partially deactivated, contacting said alkylation catalyst with an oxygen-containing gas at a temperature of about 120 to about 600° C.; and then
(c) contacting the catalyst from step (b) with an aqueous medium.

Preferably, the molecular sieve of the alkylation catalyst is selected from MCM-22, PSH-3, SSZ-25, MCM-36, MCM-49, MCM-56, faujasite, mordenite and zeolite beta.

Preferably, the contacting step (a) is conducted in the liquid phase.

Preferably, the alkylating agent includes an alkylating aliphatic group having 1 to 5 carbon atoms.

Preferably, the alkylating agent is ethylene or propylene and the alkylatable aromatic compound is benzene.

DETAILED DESCRIPTION OF THE INVENTION

The present invention relates to a process for the production of a monoalkylated aromatic compound, particularly ethylbenzene or cumene, by the liquid phase alkylation of an alkylatable aromatic compound with an alkylating agent in the presence of an alkylation catalyst comprising molecular sieve. More particularly, the invention is concerned with a process in which, when the alkylation catalyst has become at least partially deactivated, the catalyst is subjected to an ex-situ catalyst regeneration step, in which the deactivated alkylation catalyst is contacted with an oxygen-containing gas at a temperature of about 120 to about 600° C. and then with an aqueous medium so as to reactivate the catalyst substantially without loss of its monoalkylation selectivity.

The term "aromatic" in reference to the alkylatable compounds which are useful herein is to be understood in accordance with its art-recognized scope which includes alkyl substituted and unsubstituted mono- and polynuclear compounds. Compounds of an aromatic character which possess a non-carbon or hetero atom are also useful provided they do not act as catalyst poisons under the reaction conditions selected.

Substituted aromatic compounds which can be alkylated herein must possess at least one hydrogen atom directly bonded to the aromatic nucleus. The aromatic rings can be substituted with one or more alkyl, aryl, alkaryl, alkoxy, aryloxy, cycloalkyl, halide, and/or other groups which do not interfere with the alkylation reaction.

Suitable aromatic hydrocarbons include benzene, naphthalene, anthracene, naphthacene, perylene, coronene, and phenanthrene, with benzene being preferred.

Generally the alkyl groups which can be present as substituents on the aromatic compound contain from 1 to about 22 carbon atoms and usually from about 1 to 8 carbon atoms, and most usually from about 1 to 4 carbon atoms.

Suitable alkyl substituted aromatic compounds include toluene, xylene, isopropylbenzene, normal propylbenzene, alpha-methylnaphthalene, ethylbenzene, cumene, mesitylene, durene, p-cymene, butylbenzene, pseudocumene, o-diethylbenzene, m-diethylbenzene, p-diethylbenzene, isoamylbenzene, isohexylbenzene, pentaethylbenzene, pentamethylbenzene; 1,2,3,4-tetraethylbenzene; 1,2,3,5-tetramethylbenzene; 1,2,4-triethylbenzene; 1,2,3-trimethylbenzene, m-butyltoluene; p-butyltoluene; 3,5-diethyltoluene; o-ethyltoluene; p-ethyltoluene; m-propyltoluene; 4-ethyl-m-xylene; dimethylnaphthalenes; ethylnaphthalene; 2,3-dimethylanthracene; 9-ethylanthracene; 2-methylanthracene; o-methylanthracene; 9,10-dimethylphenanthrene; and 3-methyl-phenanthrene. Higher molecular weight alkylaromatic hydrocarbons can also be used as starting materials and include aromatic hydrocarbons such as are produced by the alkylation of aromatic hydrocarbons with olefin oligomers. Such products are frequently referred to in the art as alkylate and include hexylbenzene, nonylbenzene, dodecylbenzene, pentadecylbenzene, hexyltoluene, nonyltoluene, dodecyltoluene, pentadecytoluene, etc. Very often alkylate is obtained as a high boiling fraction in which the alkyl group attached to the aromatic nucleus varies in size from about $C_6$ to about $C_{12}$. When cumene or ethylbenzene is the desired product, the present process produces acceptably little by-products such as xylenes. The xylenes make in such instances may be less than about 500 ppm.

Reformate containing substantial quantities of benzene, toluene and/or xylene constitutes a particularly useful feed for the alkylation process of this invention.

The alkylating agents which are useful in the process of this invention generally include any aliphatic or aromatic organic compound having one or more available alkylating aliphatic groups capable of reaction with the alkylatable aromatic compound, preferably with the alkylating group possessing from 1 to 5 carbon atoms. Examples of suitable alkylating agents are olefins such as ethylene, propylene, the butenes, and the pentenes; alcohols (inclusive of monoalcohols, dialcohols, trialcohols, etc.) such as methanol, ethanol, the propanols, the butanols, and the pentanols; aldehydes such as formaldehyde, acetaldehyde, propionaldehyde, butyraldehyde, and n-valeraldehyde; and alkyl halides such as methyl chloride, ethyl chloride, the propyl chlorides, the butyl chlorides, and the pentyl chlorides, and so forth.

Mixtures of light olefins are especially useful as alkylating agents in the alkylation process of this invention. Accordingly, mixtures of ethylene, propylene, butenes, and/or pentenes which are major constituents of a variety of refinery streams, e.g., fuel gas, gas plant off-gas containing ethylene, propylene, etc., naphtha cracker off-gas containing light olefins, refinery FCC propane/propylene streams, etc., are useful alkylating agents herein. For example, a typical FCC light olefin stream possesses the following composition:

|  | Wt. % | Mole % |
| --- | --- | --- |
| Ethane | 3.3 | 5.1 |
| Ethylene | 0.7 | 1.2 |
| Propane | 4.5 | 15.3 |
| Propylene | 42.5 | 46.8 |
| Isobutane | 12.9 | 10.3 |
| n-Butane | 3.3 | 2.6 |
| Butenes | 22.1 | 18.32 |
| Pentanes | 0.7 | 0.4 |

Reaction products which may be obtained from the process of the invention include ethylbenzene from the reaction of benzene with ethylene, cumene from the reaction of benzene with propylene, ethyltoluene from the reaction of toluene with ethylene, cymenes from the reaction of toluene with propylene, and sec-butylbenzene from the reaction of benzene and n-butenes.

The alkylation process of this invention is conducted such that the organic reactants, i.e., the alkylatable aromatic compound and the alkylating agent, are brought into contact with an alkylation catalyst in a suitable reaction zone such as, for example, in a flow reactor containing a fixed bed of the catalyst composition, under effective alkylation conditions. Such conditions include a temperature of from about 0° C. to about 500° C., and preferably between about 50° C. and about 250° C., a pressure of from about 0.2 to about 250 atmospheres, and preferably from about 5 to about 100 atmospheres, a molar ratio of alkylatable aromatic compound to alkylating agent of from about 0.1:1 to about 50:1, and preferably can be from about 0.5:1 to about 10:1, and a feed weight hourly space velocity (WHSV) of between about 0.1 and 500 $hr^{-1}$, preferably between 0.5 and 100 $hr^{-1}$.

The reactants can be in either the vapor phase or the liquid phase and can be neat, i.e., free from intentional admixture or dilution with other material, or they can be brought into contact with the zeolite catalyst composition with the aid of carrier gases or diluents such as, for example, hydrogen or nitrogen.

When benzene is alkylated with ethylene to produce ethylbenzene, the alkylation reaction may be carried out in the liquid phase. Suitable liquid phase conditions include a temperature between 300° and 600° F. (about 150° and 316° C.), preferably between 400° F. and 500° F. (about 205° C. and 260° C.), a pressure up to about 3000 psig (20875 kPa), preferably between 400 and 800 psig (2860 and 5600 kPa), a space velocity between about 0.1 and 20 WHSV, preferably between 1 and 6 WHSV, based on the ethylene feed, and a ratio of the benzene to the ethylene in the alkylation reactor from 1:1 to 30:1 molar, preferably from about 1:1 to 10:1 molar.

When benzene is alkylated with propylene to produce cumene, the reaction may also take place under liquid phase conditions, preferably including a temperature of up to about 250° C., more preferably from a temperature up to about 150° C., still more preferably from a temperature from about 10° C. to about 125° C.; preferably including a pressure of about 250 atmospheres or less, more preferably from a pressure from about 1 to about 30 atmospheres; and an aromatic hydrocarbon weight hourly space velocity (WHSV) of from about 5 hr$^{-1}$ to about 250 hr$^1$, preferably from 5 hr$^{-1}$ to 50 hr$^{-1}$.

The alkylation catalyst comprises a crystalline molecular sieve preferably selected from MCM-22 (described in detail in U.S. Pat. No. 4,954,325), PSH-3 (described in detail in U.S. Pat. No. 4,439,409), SSZ-25 (described in detail in U.S. Pat. No. 4,826,667), MCM-36 (described in detail in U.S. Pat. No. 5,250,277), MCM-49 (described in detail in U.S. Pat. No. 5,236,575), MCM-56 (described in detail in U.S. Pat. No. 5,362,697), faujasite, mordenite, and zeolite beta (described in detail in U.S. Pat. No. 3,308,069). The molecular sieve can be combined in conventional manner with an oxide binder, such as alumina, such that the final alkylation catalyst contains between 2 and 80 wt % sieve. Alternatively, the molecular sieve can be used in self-bound form that is without a separate oxide binder.

As the alkylation process of the invention proceeds, the alkylation catalyst will gradually lose its alkylation activity, such that the reaction temperature required to achieve a given performance parameter, for example conversion of the alkylating agent, will increase. According to the invention, when the alkylation activity of the catalyst has decreased by some predetermined amount, typically 5 to 90% and, more preferably 10 to 50%, compared to the initial alkylation activity of the catalyst, the deactivated catalyst is subjected to the novel ex-situ regeneration procedure of the invention.

The regeneration procedure of the invention comprises the steps of contacting the deactivated catalyst with an oxygen-containing gas at a temperature of about 120 to about 600° C., preferably about 350 to about 525° C., and then contacting the catalyst with an aqueous medium. Preferably, the step of contacting the catalyst with an aqueous medium is conducted at a temperature of about 15 to about 120° C., more preferably about 50 to about 80° C., still more preferably about 25 to about 80° C., for a period of about 10 minutes to about 48 hours, more preferably about 30 minutes to about 4 hours. Any oxygen-containing gas can be used in the initial regeneration step, but preferably the gas is air. In addition, any aqueous medium can be used to contact the oxygen regenerated catalyst. Particularly preferred aqueous media for use in the regeneration process of the invention are aqueous solutions of ammonium carbonate, ammonium nitrate, nitric acid, hydrochloric acid, sulfuric acid, phosphoric acid, oxalic acid, salicyclic acid, propionic acid, benzoic acid, acetic acid and mixtures thereof.

Preferably, after contacting with the aqueous medium, the catalyst is optionally washed in water or in a water solution comprised of distilled, deionized or demineralized water, and then calcined at a temperature of about 25 to about 600° C. for a period of about 10 minutes to about 48 hours.

The regeneration procedure of the invention is found to be effective in restoring the activity of the catalyst without substantial loss in the monalkylation selectivity of the catalyst.

It is to be appreciated that in practice the alkylation catalyst used in the process of the invention may undergo one or more in-situ reactivation procedures, for example by stripping with a $C_1$–$C_8$ alkane, preferably propane, before being subjected to the ex-situ regeneration procedure of the invention. Such in-situ reactivation may be conveniently carried out at a temperature of about 150 to 260° C., a pressure between about 1 atm and 50 atm, a WHSV between about 0.01 and 50 hr$^{-1}$ and a time of about 0.1 hours to 30 days, more preferably from 1 to 24 hours. The regeneration process of the invention may be employed when in-situ activation is ineffective in restoring the activity of the catalyst.

The alkylation process of the invention is particularly intended to produce monoalkylated aromatic compounds, such as ethylbenzene and cumene, but the alkylation step will normally produce some polyalkylated species. Thus the process preferably includes the further steps of separating the polyalkylated species from the alkylation effluent and reacting them with additional aromatic feed in a transalkylation reactor over a suitable transalkylation catalyst. The transalkylation catalyst is preferably a molecular sieve which is selective to the production of the desired monoalkylated species and can, for example employ the same molecular sieve as the alkylation catalyst, such as MCM-22, MCM-36, MCM-49, MCM-56 and zeolite beta. In addition, the transalkylation catalyst may be ZSM-5, zeolite X, zeolite Y, and mordenite, such as TEA-mordenite.

The transalkylation reaction of the invention is conducted in the liquid phase under suitable conditions such that the polyalkylated aromatics react with the additional aromatic feed to produce additional monoalkylated product. Suitable transalkylation conditions include a temperature of 100 to 260° C., a pressure of 10 to 50 barg (200–600 kPa), a weight hourly space velocity of 1 to 10 on total feed, and benzene/polyalkylated benzene weight ratio 1:1 to 6:1.

When the polyalkylated aromatics are polyethylbenzenes and are reacted with benzene to produce ethylbenzene, the transalkylation conditions preferably include a temperature of 220 to 260° C., a pressure of 20 to 30 barg, weight hourly space velocity of 2 to 6 on total feed and benzene/PEB weight ratio 2:1 to 6:1.

When the polyalkylated aromatics are polypropylbenzenes and are reacted with benzene to produce cumene, the transalkylation conditions preferably include a temperature of 100 to 200° C., a pressure of 20 to 30 barg, weight hourly space velocity of 1 to 10 on total feed and benzene/PIPB weight ratio 1:1 to 6:1.

As the transalkylation catalyst becomes deactivated, it may be subjected to the same regeneration process as described above in relation to the alkylation catalyst.

The invention will now be more particularly described with reference to the following Examples. In the Examples, catalyst performance is defined by reference to the kinetic rate constant which is determined by assuming second order reaction kinetics. For a discussion of the determination of the kinetic rate constant, reference is directed to "Heterogeneous Reactions: Analysis, Examples, and Reactor Design, Vol. 2: Fluid-Fluid-Solid Reactions" by L. K. Doraiswamy and M. M. Sharma, John Wiley & Sons, New York (1994) and to "Chemical Reaction Engineering" by O. Levenspiel, Wiley Eastern Limited, New Delhi (1972).

EXAMPLE 1

Benzene alkylation with propylene was first conducted using an MCM-22 catalyst with 65 wt % MCM-22 crystal and 35 wt % alumina in ¹⁄₁₆" cylindrical extrudate form. One gram of the catalyst was charged to an isothermal wellmixed Parr autoclave reactor along with a mixture comprising benzene (156 g) and propylene (28 g). The reaction was carried out at 266° F. (130° C.) and 300 psig for 4 hours. A small sample of the product was withdrawn at regular intervals and analyzed by gas chromatography. The catalyst performance was assessed by a kinetic activity rate constant based on propylene conversion and cumene selectivity at 100% propylene conversion, and is listed in Table 1.

EXAMPLE 2

Benzene alkylation with propylene was then conducted using spent MCM-22 catalyst unloaded from a commercial cumene unit at the end of its cycle. One gram of this spent catalyst was evaluated for benzene alkylation with propylene in the batch test according to the procedure described in Example 1. Activity and cumene selectivity of this spent catalyst at 100% propylene conversion are listed in Table 1.

EXAMPLE 3

The spent MCM-22 catalyst from Example 2, unloaded from the commercial cumene reactor, was then regenerated ex-situ in flowing air at a gas hourly space velocity of 300 hr$^{-1}$ at 1000° F. (538° C.) for 12 hours. One gram of this air regenerated catalyst was evaluated for benzene alkylation with propylene in the batch test according to the procedure described in Example 1. Activity and cumene selectivity of this spent catalyst at 100% propylene conversion are listed described in Table 1.

EXAMPLE 4

A 1.0 molar solution of ammonium nitrate was prepared by dissolving 80 grams of ammonium nitrate (1 mole) in 1 liter of distilled water. This solution was stirred until the ammonium nitrate completely dissolved. 25 grams of air-regenerated commercial cumene catalyst from Example 3 were loaded into a 500 cc flask and 125 mL of 1 Molar ammonium nitrate solution was then added to this flask. The flask was allowed to stand for 1 hour with gentle stirring. The extrudates were then recovered by filtration, washed with 125 mL of distilled water, and then placed in a beaker. This treatment procedure was repeated one more time. Following the second wash, the extrudates were transferred to a crucible. The crucible was then placed in an oven where the extrudates were dried for 4 hours at 120° C. The extrudates were then calcined at 538° C. for 4 hours in full air. One gram of this ammonium nitrate washed catalyst was evaluated for benzene alkylation with propylene in the batch test according to the procedure described in Example 1. Activity and cumene selectivity of this spent catalyst at 100% propylene conversion are listed described in Table 1.

EXAMPLE 5

The procedure of Example 4 was repeated but in which the ammonium nitrate solution being replaced by a 0.5 molar solution of acetic acid was prepared by dissolving 30 grams of acetic acid (0.5 mole) in 1 liter of distilled water. One gram of the calcined, acetic acid washed catalyst was evaluated for benzene alkylation with propylene in the batch test according to the procedure described in Example 1. Activity and cumene selectivity of this spent catalyst at 100% propylene conversion are listed in Table 1.

EXAMPLE 6

A 0.01 molar solution of nitric acid was prepared by dissolving 0.63 grams of nitric acid (0.01 mole) in 1 liter of distilled water. This solution was stirred until the nitric acid completely dissolved. 25 grams of air-regenerated commercial cumene catalyst from Example 3 was loaded into a 500 cc beaker. 125 mL of 0.01 Molar nitric acid solution was then added to this flask. The flask was allowed to stand for 1 hour with gentle stirring. The extrudates were then recovered by filtration, washed with 125 mL of distilled water, and then placed in a beaker. This treatment procedure was then repeated using distilled water in place of the nitric acid solution. Following the second wash, the extrudates were transferred to a crucible. The crucible was then placed in an oven where the extrudates were dried for 4 hours at 120° C. One gram of this nitric acid washed and dried-only catalyst was evaluated for benzene alkylation with propylene in the batch test according to the procedure described in Example 1. Activity and cumene selectivity of this catalyst at 100% propylene conversion are listed in Table I.

EXAMPLE 7

A 0.5 molar solution of nitric acid was prepared by dissolving 31.5 grams of nitric acid (0.5 mole) in 1 liter of distilled water. This solution was stirred until the nitric acid completely dissolved. 25 grams of air-regenerated commercial cumene catalyst from Example 3 was loaded into a 500 cc beaker. 125 mL of 0.5 Molar nitric acid solution was then added to this flask. The flask was allowed to stand for 1 hour with gentle stirring. The extrudates were then recovered by filtration, washed with 125 mL of distilled water, and then placed in a beaker. This treatment procedure was then repeated using distilled water in place of the nitric acid solution. Following the second wash, the extrudates were transferred to a crucible. The crucible was then placed in an oven where the extrudates were dried for 4 hours at 120° C. One gram of this nitric acid washed and dried-only catalyst was evaluated for benzene alkylation with propylene in the batch test according to the procedure described in Example 1. Activity and cumene selectivity of this catalyst at 100% propylene conversion are listed in Table 1.

TABLE 1

| Catalyst | Cumene Activity | DiPB/ Cumene (%) | % Increase in Total Polyalkylate Make |
|---|---|---|---|
| Example 1 Fresh MCM-22 Catalyst | 80 | 16.5 | — |
| Example 2 Spent MCM-22 Catalyst | 42 | 16.3 | NIL |
| Example 3 Air Regenerated MCM-22 Catalyst | 77 | 22.5 | 36 |
| Example 4 Air Regenerated Catalyst of Example 3, followed by washing with ammonium nitrate | 90 | 16.4 | NIL |
| Example 5 Air Regenerated Catalyst of Example 3, followed by washing with acetic acid | 85 | 16.2 | NIL |
| Example 6 Air Regenerated Catalyst of Example 3, followed by washing with 0.01 M nitric acid solution | 79 | 16.0 | NIL |
| Example 7 Air Regenerated Catalyst of Example 3, followed by washing with 0.5 M nitric acid solution | 77 | 15.5 | NIL |

The performance of fresh MCM-22 catalyst is compared to various MCM-22 catalysts from Examples 2 through 7 in Table 1 above. The data represent kinetic rate constants evaluated based upon propylene conversion as well as cumene selectivity measured as the amount of diisopropylbenzene formed per unit amount of cumene produced according to the procedure outlined in Example 1. It will be seen from Table 1 that the regeneration procedure of the invention, in which the air burning is followed by aqueous treatment (Examples 4 through 7), gave improved activity restoration and improved mono-selectivity retention as compared with the prior art process of air regeneration alone (Example 3).

What is claimed is:

1. A process for regeneration of a spent aromatics alkylation or transalkylation catalyst comprising a molecular sieve, the process comprising the steps of contacting the spent catalyst with an oxygen-containing gas at a temperature of about 120 to about 600° C. and then contacting the catalyst with an aqueous medium selected from the group consisting of an ammonium nitrate solution, an ammonium carbonate solution, a nitric acid solution, a hydrochloric acid solution, a sulfuric acid solution, a phospheric acid solution, an oxalic acid solution, a salicyclic acid solution, a propionic acid solution, a benzoic acid solution and mixtures thereof.

2. The process of claim 1 wherein the step of contacting the catalyst with an aqueous medium is conducted at a temperature of about 15 to about 120° C. for a period of about 10 minutes to about 48 hours.

3. The process of claim 1 wherein, after contacting with the aqueous medium, the catalyst is calcined at a temperature of about 25 to about 600° C. for a period of about 10 minutes to about 48 hours.

4. A process for alkylating an aromatic compound comprising the steps of:
   (a) contacting an alkylatable aromatic compound and an alkylating agent with an alkylation catalyst comprising a molecular sieve under alkylation conditions; and
   (b) when said alkylation catalyst has become at least partially deactivated, contacting said alkylation catalyst with an oxygen-containing gas at a temperature of about 120 to about 600° C.; and then
   (c) contacting the catalyst from step (b) with an aqueous medium, selected from the group consisting of a nitric acid solution, a hydrochloric acid solution, a sulfuric acid solution, a phosphoric acid solution, an oxalic acid solution, a salicyclic acid solution, a propionic acid solution, a benzoic acid solution and mixtures thereof.

5. The process of claim 4 wherein the contacting step (a) is conducted in the liquid phase.

6. The process of claim 4 wherein the alkylating agent includes an alkylating aliphatic group having 1 to 5 carbon atoms.

7. The process of claim 4 wherein the alkylating agent is ethylene or propylene and the alkylatable aromatic compound is benzene.

8. The process of claim 4 wherein the molecular sieve of the alkylation catalyst of step (a) is selected from MCM-22, PSH-3, SSZ-25, MCM-36, MCM-49, MCM-56, faujasite, mordenite and zeolite beta.

9. The process of claim 4 wherein the step of contacting the catalyst with an aqueous medium is conducted at a temperature of about 15 to about 120° C. for a period of about 10 minutes to about 48 hours.

10. The process of claim 4 including the further step, after step (c), of calcining the catalyst at a temperature of about 25 to about 600° C. for a period of about 10 minutes to about 48 hours.

11. A process for regeneration of a spent aromatics alkylation or transalkylation catalyst comprising a molecular sieve, the process comprising the steps of:
   (a) contacting the spent catalyst with an oxygen-containing gas at a temperature of about 120 to about 600° C.;
   (b) contacting the spent catalyst with an aqueous medium selected from the group consisting of an ammonium nitrate solution, an ammonium carbonate solution, a nitric acid solution, a hydrochloric acid solution, a sulfuric acid solution, a phosphoric acid solution, an oxalic acid solution, a salicyclic acid solution, a propionic acid solution, a benzoic acid solution, an acetic acid solution and mixtures therof; and
   (c) contacting the spent catalyst with water or a water solution.

12. The process of claim 11 including the further step, after step (c) of calcining the catalyst at a temperature of about 25 to about 600° C. for a period of about 10 minutes to about 48 hours.

* * * * *